US006777580B2

(12) United States Patent
Devine et al.

(10) Patent No.: US 6,777,580 B2
(45) Date of Patent: *Aug. 17, 2004

(54) PROCESS FOR THE SYNTHESIS OF (R)-1-(3, 5-BIS(TRIFLUOROMETHYL)-PHENYL) ETHAN-1-OL BY ASYMMETRIC TRANSFER HYDROGENATION

(75) Inventors: Paul Devine, Lincroft, NJ (US); Hansen Karl, Atlantic Highlands, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/324,956

(22) Filed: Dec. 20, 2002

(65) Prior Publication Data

US 2003/0153760 A1 Aug. 14, 2003

Related U.S. Application Data

(62) Division of application No. 09/607,229, filed on Jun. 30, 2000, now Pat. No. 6,504,066.
(60) Provisional application No. 60/141,988, filed on Jul. 1, 1999, and provisional application No. 60/161,957, filed on Oct. 28, 1999.

(51) Int. Cl.$^7$ ................................................ C07C 33/46
(52) U.S. Cl. ....................................................... 568/812
(58) Field of Search .................................. 568/812, 814

(56) References Cited

U.S. PATENT DOCUMENTS

| 4,290,961 | A | * | 9/1981 | Mestroni |
| 5,763,688 | A | * | 6/1998 | Ikariya |
| 6,184,381 | B1 | * | 2/2001 | Ikariya |
| 6,372,931 | B1 | * | 4/2002 | Blacker |
| 6,504,066 | B1 | * | 1/2003 | Devine |

FOREIGN PATENT DOCUMENTS

| JP | 11-124350 | * | 5/1999 |
| WO | WO-98/42643 | * | 10/1998 |

* cited by examiner

Primary Examiner—Michael L. Shippen
(74) Attorney, Agent, or Firm—J. Eric Thies; Melvin Winokur

(57) ABSTRACT

The present invention is concerned with novel processes for the preparation of (R)-1-(3,5-bis(trifluoromethyl)phenyl) ethan-1-ol. This compound is useful as an intermediate in the synthesis of compounds which possess pharmacological activity.

6 Claims, No Drawings

PROCESS FOR THE SYNTHESIS OF (R)-1-(3, 5-BIS(TRIFLUOROMETHYL)-PHENYL) ETHAN-1-OL BY ASYMMETRIC TRANSFER HYDROGENATION

CROSS REFERENCE TO RELATED APPLICATIONS

This application is a division of copending application Ser. No. 09/607,229, filed Jun. 30, 2000 now U.S. Pat. No. 6,504,066, which claims priority under 35 U.S.C. §119(e) from Provisional Application No. 60/141,988, filed Jul. 1, 1999, and Provisional Application No. 60/161,957, filed Oct. 28, 1999.

BACKGROUND OF THE INVENTION

The present invention relates to processes for the preparation of (R)-1-(3,5-bis(trifluoromethyl)phenyl)ethan-1-ol which is useful as an intermediate in the preparation of certain therapeutic agents. In particular, the present invention provides a process for the preparation of (R)-1-(3,5-bis (trifluoromethyl)phenyl)ethan-1-ol which is an intermediate in the synthesis of pharmaceutical compounds which are substance P (neurokinin-1) receptor antagonists.

The (R)-1-(3,5-bis(trifluoromethyl)phenyl)ethan-1-ol prepared by the present invention may be utilized in the synthesis of (2R, 2-alpha-R, 3a)-2-[1-[3,5-bis (trifluoromethyl)phenyl]ethoxy-3-(4-fluorophenyl)-1,4-oxazine of the formula:

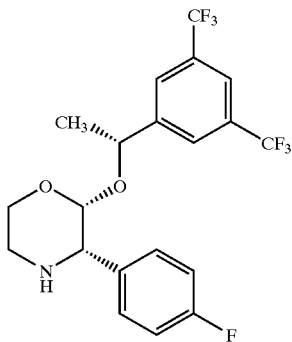

which is a known intermediate in the synthesis of pharmaceutical compounds which are substance P (neurokinin-1) receptor antagonists.

The general processes disclosed in the art for the preparation of (R)-1-(3,5-bis(trifluoromethyl)phenyl)ethan-1-ol result in relatively low and inconsistent yields of the desired product. In contrast to the previously known processes, the present invention provides effective methodology for the preparation of (R)-1-(3,5-bis(trifluoromethyl)phenyl)ethan-1-ol in relatively high yield and enantiomeric purity.

It will be appreciated that (R)-1-(3,5-bis(trifluoromethyl) phenyl)ethan-1-ol is an important intermediate for a particularly useful class of therapeutic agents. As such, there is a need for the development of a process for the preparation of (R)-1-(3,5-bis(trifluoromethyl)phenyl)ethan-1-ol which is readily amenable to scale-up, uses cost-effective and readily available reagents and which is therefore capable of practical application to large scale manufacture.

Accordingly, the subject invention provides a process for the preparation of (R)-1-(3,5-bis(trifluoromethyl)phenyl) ethan-1-ol via a very simple, short and highly efficient synthesis.

SUMMARY OF THE INVENTION

The novel process of this invention involves the synthesis of (R)-1-(3,5-bis(trifluoromethyl)phenyl)ethan-1-ol. In particular, the present invention is concerned with novel processes for the preparation of a compound of the formula:

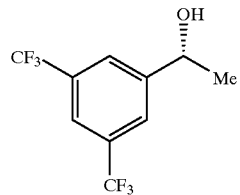

This compound is an intermediate in the synthesis of compounds which possess pharmacological activity. In particular, such compounds are substance P (neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of (R)-1-(3,5-bis(trifluoromethyl)phenyl)ethan-1-ol of the formula:

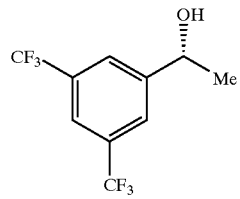

An embodiment of the general process for the preparation of (R)-1-(3,5-bis(trifluoromethyl)phenyl)ethan-1-ol is as follows:

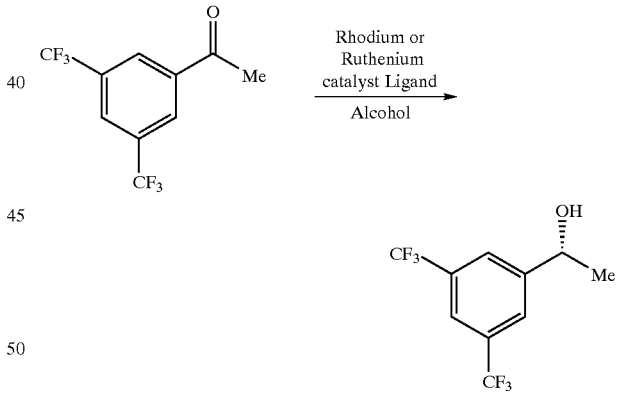

In accordance with this embodiment of the present invention, the treatment of 1-(3,5-bis(trifluoromethyl)-phenyl)ethan-1-one with a rhodium or a ruthenium catalyst and a ligand in the presence of an alcohol provides (R)-1-(3,5-bis(trifluoromethyl)-phenyl)ethan-1-ol in higher yields, in greater entantiomeric purity and in a more efficient route than the processes disclosed in the art.

In another embodiment, the present invention is directed to a process for the preparation of (R)-1-(3,5-bis (trifluoromethyl)phenyl)ethan-1-ol which comprises the treatment of 1-(3,5-bis(trifluoromethyl)-phenyl)ethan-1-one with a rhodium a ruthenium catalyst and a ligand in the presence of an alcohol to give (R)-1-(3,5-bis (trifluoromethyl)phenyl)ethan-1-ol.

A specific embodiment of the present invention concerns a process for the preparation of (R)-1-(3,5-bis(trifluoromethyl)phenyl)ethan-1-ol of the formula:

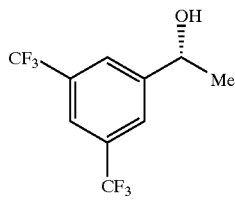

which comprises:
treating 1-(3,5-bis(trifluoromethyl)phenyl)ethan-1-one of the formula:

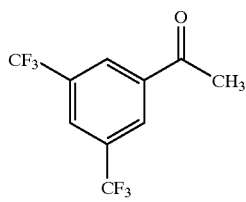

with a rhodium or a ruthenium catalyst and a ligand in the presence of an alcohol;
to give (R)-1-(3,5-bis(trifluoromethyl)phenyl)ethan-1-ol of the formula:

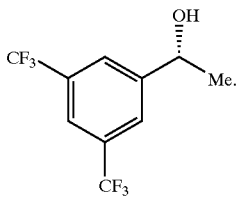

In the present invention, it is preferred that the rhodium catalyst is selected from bis((pentamethylcyclopentadienyl)rhodium chloride) (i.e. ((pentamethylcyclopentadienyl)RhCl$_2$)$_2$) and bis((cyclopentadienyl)rhodium chloride) (i.e. ((cyclopentadienyl)RhCl$_2$)$_2$). The preferred rhodium catalyst is bis((pentamethylcyclopentadienyl)rhodium chloride). The rhodium catalyst is preferably present at a concentration of about 0.1–1 mol % and more preferably about 0.5 mol %.

In the present invention, it is preferred that the ruthenium catalyst is selected from bis((4-isopropyl-toluenyl)ruthenium chloride) and bis((cyclopentadienyl)ruthenium chloride). The preferred ruthenium catalyst is bis((4-isopropyl-toluenyl)ruthenium chloride) [i.e. bis((para-cymenyl)ruthenium chloride))]. The ruthenium catalyst is preferably present at a concentration of about 0.1–1 mol % and more preferably about 0.3 mol %.

To minimize expense, the use of a ruthenium catalyst is preferred.

In the present invention, it is preferred that the ligand is selected from (R,R)-cyclohexane diamine (R,R)CHXD, pseudoephedrine, nor-pseudoephedrine, ephedrine, nor-ephedrine and (S,R)-cis-1-amino-2-hydroxy-indane. In the present invention, it is more preferred that the ligand is (S,R)-cis-1-amino-2-hydroxy-indane. The ligand is preferably present at a concentration of about 0.1–1 mol % and more preferably about 0.5 mol %.

For convenience, the rhodium or ruthenium catalyst and the ligand may be contacted together in situ. In the present invention the rhodium or ruthenium catalyst and the ligand optionally may be contacted together to form a catalyst-ligand complex prior to reaction with (R)-1-(3,5-bis(trifluoromethyl)phenyl)ethan-1-ol.

In an alternate embodiment, the present invention is directed to a compound which is:

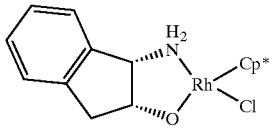

wherein Cp* is pentamethylcyclopentadienyl.

In an alternate embodiment, the present invention is directed to a compound which is:

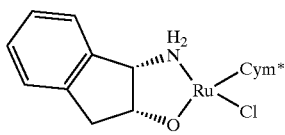

wherein Cym* is p-cymene (4-isopropyl-toluene).

In the present invention, it is preferred that the alcohol is selected from methanol, ethanol, isopropanol, isobutanol or n-butanol. The most preferred alcohol is isopropanol. Although other solvents may also be present, for convenience it is preferred that the alcohol is employed as a solvent for the conducting the reaction.

In the present invention a base is optionally present with the alcohol. The base may be an inorganic base such as a base selected from potassium or sodium hydroxide, potassium or sodium carbonate, potassium or sodium bicarbonate potassium or sodium alkoxides, and the like. The alkoxides can be derived from lower ($C_1$–$C_5$) or higher (>$C_6$) primary, secondary or tertiary alcohols. A preferred base is sodium hydroxide.

The (R)-1-(3,5-bis(trifluoromethyl)phenyl)ethan-1-ol obtained in accordance with the present invention may be used as starting material in further reactions directly or following purification.

In an alternate embodiment, the present invention is directed to a process for purification or enhancing the enantiomeric purity of (R)-1-(3,5-bis(trifluoromethyl)-phenyl)ethan-1-ol which comprises:
  contacting (R)-1-(3,5-bis(trifluoromethyl)phenyl)ethan-1-ol with 1,4-diazabicyclo[2.2.2]octane in an organic solvent to form bis-((R)-1-(3,5-bis(trifluoromethyl)phenyl)ethan-1-ol)1,4-diazabicyclo[2.2.2]octane;
  recovering the bis-((R)-1-(3,5-bis(trifluoromethyl)phenyl)ethan-1-ol)1,4-diazabicyclo[2.2.2]octane;
  and optionally dissociating the 1,4-diazabicyclo[2.2.2]octane from the bis-((R)-1-(3,5-bis(trifluoromethyl)phenyl)ethan-1-ol)1,4-diazabicyclo[2.2.2]octane to give (R)-1-(3,5-bis(trifluoromethyl)phenyl)ethan-1-ol.

In this process, it is preferred that the organic solvent is an alkane, it is more preferred that the organic solvent is selected from: hexane and heptane and it is even more preferred that the organic solvent is heptane.

The diazabicyclo[2.2.2]octane is preferably present at a ratio of 0.5 equivalents of diazabicyclo[2.2.2]octane to 1.0 equivalents of (R)-1-(3,5-bis(trifluoromethyl)phenyl)ethan-1-ol.

The diazabicyclo[2.2.2]octane is preferably present at a concentration of about 0.05–1 mol % and more preferably about 0.5 mol %.

Optionally, the mixture is seeded with bis-((R)-1-(3,5-bis (trifluoromethyl)phenyl)ethan-1-ol)1,4-diazabicyclo[2.2.2] octane after contacting (R)-1-(3,5-bis(trifluoromethyl) phenyl)ethan-1-ol with 1,4-diazabicyclo[2.2.2]octane in the organic solvent. The temperature in the formation of bis-((R)-1-(3,5-bis(trifluoromethyl)phenyl)ethan-1-ol)1,4-diazabicyclo[2.2.2]octane is preferably about 50° C. to about −40° C., more preferably about 40° C. to about −20° C., and even more preferably about 0° C. to about −20° C.

It will be appreciated by those skilled in the art that this alternate embodiment may be repeated in an itterative manner to further enhance the enantiomeric purity of (R)-1-(3, 5-bis(trifluoromethyl)-phenyl)ethan-1-ol with each subsequent cycle.

In an aspect of this alternate embodiment, the present invention is directed to a compound which is:

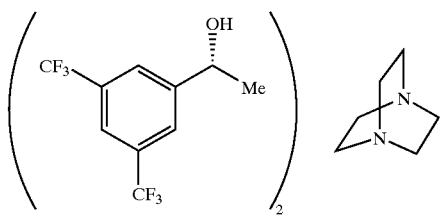

Another aspect of this alternate embodiment is directed to (R)-1-(3,5-bis(trifluoromethyl)phenyl)ethan-1-ol which is present in an enantiomeric purity (enantiomeric excess) of greater than 90%, preferably greater than 95%, more preferably greater than 98%, particularly greater than 99% and especially greater than 99.5% (enantiomeric excess).

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

3,5-Bis(trifluoromethyl)bromobenzene

| Materials | MW | Density | Amount | Mmol | Equiv. |
|---|---|---|---|---|---|
| 1,3-Bis(trifluoro-methyl)benzene | 214.1 | 1.38 | 107 g | 500 | 1.0 |
| 96% H₂SO₄ | | | 142 mL | | |
| Glacial HOAc | | | 22 mL | | |
| 1,3-Dibromo-5,5-dimethylhydantoin | 285.93 | | 77.25 g | 270 | 1.08 (Br⁺) |
| 5N Aq NaOH | | | 75 mL | | |

To glacial acetic acid (22.0 mL), cooled to 15° C. in a 1 L 3-neck round bottom flask (equipped with mechanical stirrer, thermocouple, and addition funnel), was added concentrated (96%) sulfuric acid (142 mL) in one portion. An exothermic heat of solution raised the temperature to 35° C. After cooling to 25° C., 1,3-bis(trifluoro-methyl)benzene (107 g, 500 mmol) was added. With the acid mixture rapidly stirring, 1,3-dibromo-5,5-dimethylhydantoin (77.25 g; 270 mmol) was added over 2 min to give a multiple phase mixture (solid and two liquid). An exothermic reaction occured that raised the internal temperature to ~40° C. (jacket cooling at 15° C). After the reaction temperature began to drop (after 5 min) the reaction mixture was maintained at 45° C. for 4.5 hr.

The rate and selectivity of the bromination is highly dependent on the agitation of the two phase reaction. Slower stirring increases the amount of bis-bromination and slows the overall rate of reaction. The reaction mixture remains heterogeneous throughout the reaction and the organic phase separates when agitation is interrupted. At the end of the reaction, the phases separate slowly (bromide density= 1.699). The rate of bromination is also dependent on the ratio of acetic to sulfuric acid.

Progress of the reaction is monitored by GC analysis, as follows.

Sample: ~50 µl of mixed phase, dilute with cyclohexane (1.5 mL), wash with water (1 mL), then 2N NaOH (1 mL), separate and inject.

Resteck RTX-1701 [60 meter×0.320 mm]: 100° C.; ramp: 5° C./min to 200° C.; 200° C. for 10 min; Flow 1.15 mL/min R$_t$:1,3-bis(trifluoromethyl)benzene: 7.0 min 3,5-bis(trifluoromethyl)bromobenzene: 9.4 min Biaryl: 19.2 min The mixture was cooled to 2° C. and poured slowly into cold water (250 mL). The mixture was stirred vigorously for 10 min, allowed to settle, and the lower organic layer was separated and washed with 5N NaOH (75 mL) to give 145.1 g of a clear, colorless organic layer.

The assay yield of 1,3-bis(trifluoromethyl)bromobenzene was 93.7% (137.3 g, 469 mmol), which contained 0.6% 1,3-bis(trifluoromethyl)benzene, 1.0% 1,2-dibromo-3,5-bis (trifluoromethyl)benzene, and 0.3% 1,4-dibromo-3,5-bis-(trifluoromethyl)benzene. Total isomer byproducts measured by GC were 2.0 mol %.

EXAMPLE 2

1-(3,5-Bis(trifluoromethyl)phenyl)ethan-1-one

| Materials | MW | Density | Amount | Mmol | Equiv |
|---|---|---|---|---|---|
| 3,5-Bis(trifluoromethyl)-bromobenzene | 293.03 | 1.699 g/L | 29.3 g | 98.0 | 1.0 |
| Magnesium granules, 20 mesh | 24.3 | | 5.10 g | | 2.1 |

-continued

[Reaction scheme: 1-bromo-3,5-bis(trifluoromethyl)benzene → 3',5'-bis(trifluoromethyl)acetophenone via 1) Mg, THF; 2) Ac₂O]

| | MW | Density | Amount | Mmol | Equiv |
|---|---|---|---|---|---|
| Acetic Anhydride | 102.1 | 1.08 g/L | 40 mL | 423 | 4.5 |
| THF (KF = 60 µg/mL) | | | 260 mL | | |
| MTBE | | | 650 mL | | |
| Water | | | 300 mL | | |
| 50% NaOH | | | 40 mL | | |
| Product | | | | | |
| 3',5'-Bis(trifluoro-methyl)acetophenone | 256.14 | | 20.3 g | 79.0 | 82% Yield |

To a 500 mL 3-neck round bottom flask equipped with an addition funnel, $N_2$ inlet, and a Teflon coated thermocouple was added magnesium granules (5.10 g, 210 mmol) and THF (200 mL). The mixture was heated to reflux. 3,5-Bis(trifluoromethyl)bromobenzene (29.3 g, 98 mmol) was dissolved in 30 mL of THF. Some bromide solution (5 mL) was added to the gently refluxing magnesium slurry over 2 minutes to initiate the Grignard reaction. Alternatively, the Grignard initiation may be conducted at 0–20° C. to minimize the loss of solvent. After Grignard initiation, the remaining bromide was added over 1 hour.

An initial induction period of 5 minutes is generally permitted. If the reaction does not initiate, another 5% charge of bromide solution is added. If the reaction still does not initiate after a bromide charge of 10%, 100 mg of iodine is added. The reaction exotherm was controlled by slowing or stopping the bromide addition if the reaction appeared too violent.

After complete bromide addition (~60 minutes), the dark brown solution was heated at gentle reflux for an additional 30 minutes.

The reaction was monitored by HPLC (sample preparation: 100 µL sample quenched into 3.5 mL of 1:1 THF:2N HCl, then diluted to 100 mL in 65:35 acetonitrile:pH 6 buffer). Grignard formation was considered complete when the bromide level is less that 1 mol %.

After cooling to ambient temperature in a water bath, the mixture was transferred via cannula to a 1 L addition funnel. THF (10 mL) was used as rinse. This solution was then added to a solution of acetic anhydride (40 mL) in THF (40 mL) maintained at −15° C. over 1 hr. The dark brown mixture was warmed to 10° C. in a water bath, and water (300 mL) was added over 3 minutes. The biphasic mixture was vigorously stirred while 50% NaOH was added dropwise over 1 hr, until a pH of 8.0 was maintained for 5 minutes. MTBE (300 mL) was added, the layers were separated and the aqueous layer was further extraced with MTBE (3×150 mL). The organic layers were combined and assayed (22.4 g ketone), then concentrated in vacuo at bath temperature of 32° C. (50–80 torr). The concentrate was then distilled at atmospheric pressure and 20.7 g (82% yield based on LC purity) of colorless oil was collected at 150–189° C., with the bulk collected at 187–189° C.

| HPLC Assay: | 97.7 LCAP |
|---|---|
| Method: | Luna C18, Acetonitrile:0.1% aq $H_3PO_4$, 75:25 to 95:5 over 20 min; maintain 5 min. |
| $R_t$ (min): | |
| Phenol | 5.2 |
| Ketone | 6.3 |
| Aromatic | 7.3 |
| Bromide | 9.7 |
| Dimer | 13.3 |
| GC Assay: | 95.5 GCAP |
| Method: | Resteck RTX-1701 [60 meter × 0.320 mm] 100° C. to 200° C. @ 5° C./min; 200° C. for 10 min; Flow 35 cm/sec constant flow. |
| $R_t$ (min): | |
| 1,3-bis(trifluoromethyl)benzene | 4.4 |
| Acetic anhydride | 5.6 |
| Methyl Ketone | 10.6 |
| 3,5-bis(trifluoromethyl)bromobenzene | 6.2 |
| Bis adduct | 19.6 |

EXAMPLE 3

(R)-1-(3,5-Bis(trifluoromethyl)phenyl)ethan-1-ol

[Reaction scheme showing conversion of 1-(3,5-bis(trifluoromethyl)phenyl)ethan-1-one to (R)-1-(3,5-bis(trifluoromethyl)phenyl)ethan-1-ol using Cp*Rh catalyst with (S,R)-cis-aminoindanol ligand, IPA, NaOH, and DABCO]

| | | | |
|---|---|---|---|
| 1-(3,5-Bis(trifluoromethyl)-phenyl)ethan-1-one | 256.15 | 3.9 | 1 Kg |
| (Cp*RhCl₂)₂ (Cp* = Pentamethylcyclopentadienyl) | 618.08 | 0.01 | 6 g |
| (S,R)-cis-Aminoindanol | 149.20 | 0.02 | 3.0 g |
| NaOH | 5N ($H_2O$) | 0.05 | 9 mL |
| IPA | | | 7 L |
| HCl | 1N ($H_2O$) | | 7 L |
| Heptane | | | 7 L |
| 1,4-diazabicyclo[2.2.2]octane (DABCO) | 112.18 | 2.2 | 240 g |

Rhodium salt and ligand were added to IPA at RT and aged 0.5 h. The solution generally turned bright orange over the age period. Ketone followed by base were then added and the reaction was aged until complete by HPLC (~3 h). The reaction was then quenched with 1 N HCl and extracted with heptane (2×3.5 L) and washed with 5 L brine. DABCO was added and the solution was concentrated to a volume of ~4 mL/g of alcohol. At this point the KF was less than 200 and less than 5% IPA remains. The reaction can be flushed with additional heptane if these criteria are not met. Optionally, the reaction was seeded with the DABCO complex at 40° C. and the reaction was allowed to slowly cool to RT. Crystallization began to occur immediately. The reaction was then cooled to 0° C. and filtered. The cake was washed with cold heptane. The DABCO complex was isolated in ~70% yield with an enatiomeric excess of ~99%.

EXAMPLE 4

(R)-1-(3,5-Bis(trifluoromethyl)phenyl)ethan-1-ol

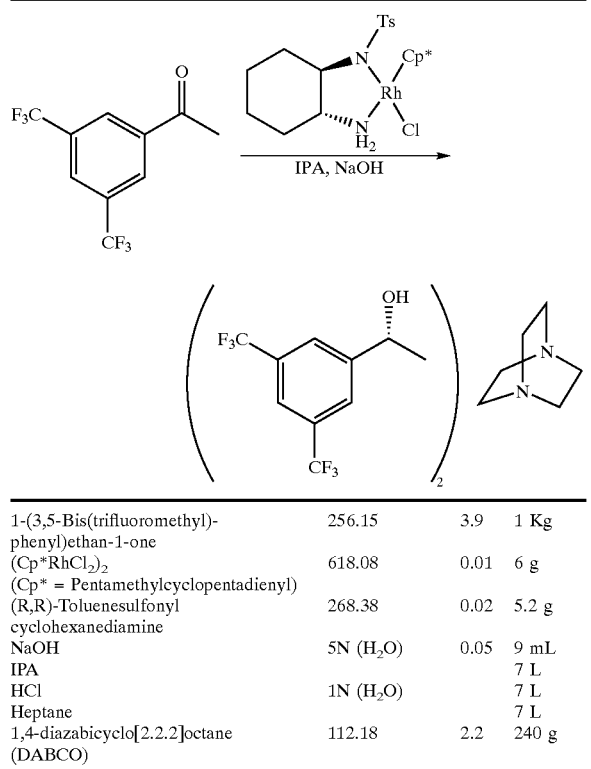

| | | | |
|---|---|---|---|
| 1-(3,5-Bis(trifluoromethyl)-phenyl)ethan-1-one | 256.15 | 3.9 | 1 Kg |
| (Cp*RhCl$_2$)$_2$ (Cp* = Pentamethylcyclopentadienyl) | 618.08 | 0.01 | 6 g |
| (R,R)-Toluenesulfonyl cyclohexanediamine | 268.38 | 0.02 | 5.2 g |
| NaOH | 5N (H$_2$O) | 0.05 | 9 mL |
| IPA | | | 7 L |
| HCl | 1N (H$_2$O) | | 7 L |
| Heptane | | | 7 L |
| 1,4-diazabicyclo[2.2.2]octane (DABCO) | 112.18 | 2.2 | 240 g |

Rhodium salt and ligand were added to IPA at RT and aged 0.5 h. The solution generally turned bright orange over the age period. Ketone followed by base were then added and the reaction was aged until complete by HPLC (~3 h). The reaction was then quenched with 1 N HCl and extracted with heptane (2×3.5 L) and washed with 5 L brine. DABCO was added and the solution was concentrated to a volume of ~4 mL/g of alcohol. At this point the KF was less than 200 and less than 5% IPA remains. The reaction can be flushed with additional heptane if these criteria are not met. Optionally, the reaction was seeded with the DABCO complex at 40° C. and the reaction was allowed to slowly cool to RT. Crystallization began to occur immediately. The reaction was then cooled to 0° C. and filtered. The cake was washed with cold heptane. The DABCO complex was isolated in ~75% yield with an enatiomeric excess of ~99.5%. The (R,R)-toluenesulfonyl cyclohexanediamine was prepared by reacting tosyl chloride with (R,R)-diaminocylcohexane. The product was isolated in 40–50% yield.

EXAMPLE 5

(R)-1-(3,5-Bis(trifluoromethyl)phenyl)ethan-1-ol

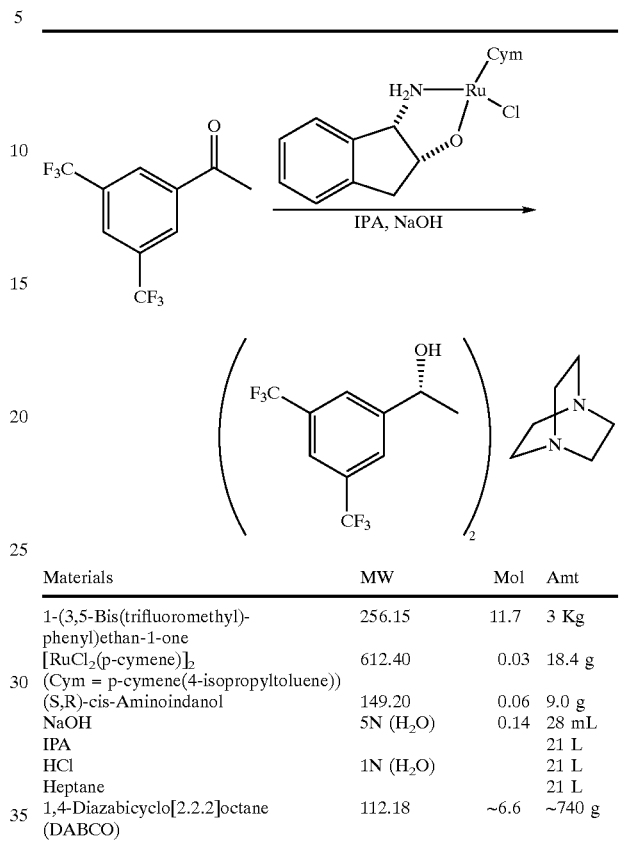

| Materials | MW | Mol | Amt |
|---|---|---|---|
| 1-(3,5-Bis(trifluoromethyl)-phenyl)ethan-1-one | 256.15 | 11.7 | 3 Kg |
| [RuCl$_2$(p-cymene)]$_2$ (Cym = p-cymene(4-isopropyltoluene)) | 612.40 | 0.03 | 18.4 g |
| (S,R)-cis-Aminoindanol | 149.20 | 0.06 | 9.0 g |
| NaOH | 5N (H$_2$O) | 0.14 | 28 mL |
| IPA | | | 21 L |
| HCl | 1N (H$_2$O) | | 21 L |
| Heptane | | | 21 L |
| 1,4-Diazabicyclo[2.2.2]octane (DABCO) | 112.18 | ~6.6 | ~740 g |

The ruthenium salt [RuCl$_2$(P-Cymene)]$_2$ and (S,R)-cis-aminoindanol were added to IPA at RT and aged 0.5 h. The solution generally turned bright yellow-orange over the age period. 1-(3,5-Bis(trifluoromethyl)phenyl)ethan-1-one was added and the reaction was degassed under vacuum. Base was then added and the reaction was aged until >98% complete by HPLC (4–6h). The reaction was then quenched by pouring it into 1 N HCl and extracted with heptane (2×10.5 L) and washed with 15 L brine. 1,4-Diazabicyclo[2.2.2]octane (DABCO) was added and the solution was concentrated to a volume of ~4 mL/g of alcohol. At this point the KF was less than 200 and less than 5% IPA remains. The reaction can be flushed with additional heptane if these criteria are not met. Optionally, the reaction was seeded with the DABCO complex at 40° C. and the reaction was allowed to slowly cool to RT. Crystallization began to occur immediately. The reaction was then cooled to 0° C. and filtered. The cake was washed with cold heptane. The DABCO complex was isolated in 75–80% yield with an enantiomeric excess of >99%.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

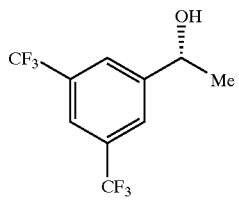

which comprises:

treating a compound of the formula:

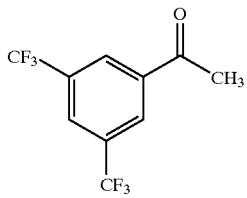

with a ruthenium catalyst which is bis((4-isopropyl-toluenyl)ruthenium chloride) and a chiral ligand which is (S,R)-cis-1-amino-2-hydroxy-indane under asymmetric transfer hydrogenation conditions and in the presence of an alcohol; to give the compound of the formula:

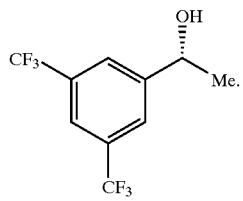

2. The process of claim 1 wherein the ruthenium catalyst is present at a concentration of about 0.1–1 mol %.

3. The process of claim 1 wherein the ligand is present at a concentration of about 0.1–1 mol %.

4. The process of claim 1 wherein the alcohol is selected from methanol, ethanol, isopropanol, isobutanol or n-butanol.

5. The process of claim 4 wherein the alcohol is isopropanol.

6. The process of claim 1 wherein sodium hydroxide is present with the alcohol.

* * * * *